(12) United States Patent
Falch et al.

(10) Patent No.: US 10,869,140 B2
(45) Date of Patent: Dec. 15, 2020

(54) DETERMINATION OF ROOM REVERBERATION FOR SIGNAL ENHANCEMENT

(71) Applicant: MED-EL Elektromedizinische Geraete GmbH, Innsbruck (AT)

(72) Inventors: Cornelia Falch, Rum (AT); Ernst Aschbacher, Innsbruck (AT); Florian Frühauf, Rinn (AT); Thomas Schwarzenbeck, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/512,877

(22) PCT Filed: Sep. 25, 2015

(86) PCT No.: PCT/US2015/052117
§ 371 (c)(1),
(2) Date: Mar. 21, 2017

(87) PCT Pub. No.: WO2016/049403
PCT Pub. Date: Mar. 31, 2016

(65) Prior Publication Data
US 2017/0303053 A1    Oct. 19, 2017

Related U.S. Application Data

(60) Provisional application No. 62/055,701, filed on Sep. 26, 2014.

(51) Int. Cl.
*H04R 25/00*    (2006.01)
*G10L 21/02*    (2013.01)
(Continued)

(52) U.S. Cl.
CPC ....... *H04R 25/505* (2013.01); *A61N 1/36036* (2017.08); *G10L 21/02* (2013.01);
(Continued)

(58) Field of Classification Search
CPC .... H04R 25/505; H04R 25/554; H04R 25/50; H04R 225/43; H04R 225/67; H04R 225/47; H04R 225/55
(Continued)

(56) References Cited

U.S. PATENT DOCUMENTS

2009/0208043 A1    8/2009 Woods et al.
2011/0255702 A1*  10/2011 Jensen ................... G01H 7/00
                                                          381/66
(Continued)

FOREIGN PATENT DOCUMENTS

EP    2381700    10/2011
JP    2006287445    10/2006

OTHER PUBLICATIONS

Lebart et al., *A new method based on spectral subtraction for speech dereverberation*, Acta Acustica united with Acustica 87.3 (2001): 359-366.
(Continued)

*Primary Examiner* — Mallika D Fairchild
*Assistant Examiner* — Minh Duc G Pham
(74) *Attorney, Agent, or Firm* — Sunstein LLP (57) ABSTRACT

A hearing prosthesis arrangement is described for a hearing assisted patient. A microphone senses an acoustic environment around the hearing assisted patient and generates a corresponding microphone output signal. An audio signal processor processes the microphone output signal and produces a corresponding prosthesis stimulation signal to the patient for audio perception. The audio signal processor includes a dereverberation process that measures a dedicated
(Continued)

reverberation reference signal produced in the acoustic environment to determine reverberation characteristics of the acoustic environment, and reduces reverberation effects in the hearing prosthesis stimulation signal based on the reverberation characteristics.

8 Claims, 6 Drawing Sheets (51) Int. Cl.
*A61N 1/36* (2006.01)
*H04R 27/00* (2006.01)
*G10L 21/0208* (2013.01)

(52) U.S. Cl.
CPC ........... *H04R 25/50* (2013.01); *H04R 25/554* (2013.01); *G10L 2021/02082* (2013.01); *H04R 27/00* (2013.01); *H04R 2225/41* (2013.01); *H04R 2225/43* (2013.01); *H04R 2225/55* (2013.01); *H04R 2225/67* (2013.01); *H04R 2227/007* (2013.01)

(58) Field of Classification Search
USPC .......................................................... 607/57
See application file for complete search history.

(56) References Cited

U.S. PATENT DOCUMENTS

2014/0025287 A1  1/2014  Christensen et al.
2015/0030170 A1*  1/2015  Fitz ........................ H04R 25/70
                                                                381/60

OTHER PUBLICATIONS

Ratnam et al., *Blind estimation of reverberation time*, The Journal of the Acoustical Society of America 114.5 (2003): 2877-2892.
Wu et al., *A pitch-based method for the estimation of short reverberation time*, Acta Acustica united with Acustica 92.2 (2006): 337-339.
Habets, *Single- and multi-microphone speech dereverberation using spectral enhancement*, Dissertation Abstracts International 68.04 (2007).
Wen et al., *Blind estimation of reverberation time based on the distribution of signal decay rates*, Acoustics, Speech and Signal Processing, 2008. ICASSP 2008. IEEE International Conference on. IEEE, 2008.
Löllman et al., *Estimation of the reverberation time in noisy environments*, Proc. of Intl. Workshop on Acoustic Echo and Noise Control (IWAENC). 2008.
Löllman et al., *A blind speech enhancement algorithm for the suppression of late reverberation and noise*, Acoustics, Speech and Signal Processing, 2009. ICASSP 2009. IEEE International Conference on. IEEE, 2009.
Kokkinakis, *A channel-selection criterion for suppressing reverberation in cochlear implants*, The Journal of the Acoustical Society of America 129.5 (2011): 3221-3232.
López et al., *Low variance blind estimation of the reverberation time*, Acoustic Signal Enhancement; Proceedings of IWAENC 2012; International Workshop on. VDE, 2012.
International Search Report/Written Opinion in International Application No. PCT/US2015/052117, dated Dec. 29, 2015, 38 pages.

* cited by examiner

DETERMINATION OF ROOM REVERBERATION FOR SIGNAL ENHANCEMENT

This application is a national phase entry of Patent Cooperation Treaty Application PCT/US2015/052117, filed Sep. 25, 2015, which in turn claims priority from U.S. Provisional Patent Application 62/055,701, filed Sep. 26, 2014, both of which are incorporated herein by reference in their entireties.

TECHNICAL FIELD

The present invention relates to signal enhancement in reverberant environments, and more particularly, to signal dereverberation for hearing assistance devices, such as a hearing aid or a cochlear implant.

BACKGROUND ART

The acoustic properties of a room, and particularly the reverberation properties, can reduce the quality of audio signals perceived by human listeners. For hearing-impaired people using hearing assistance devices such as hearing aids and cochlear implants, this problem can be particularly detrimental and result in reduced speech understanding. Even rooms of moderate size, such as class rooms or meeting rooms, can produce enough reverberation to cause hearing problems, especially for users of cochlea implant (CI) systems. See Kokkinakis et al., *A Channel-Selection Criterion for Suppressing Reverberation in Cochlear Implants*, J. Acoust. Soc. Am., vol. 129(5), 2011, which is hereby incorporated herein by reference. In larger rooms like theatres and churches, this problem can increase drastically. Dereverberation processing techniques have been used in a wide variety of signal processing applications such as mobile communication systems, tele- and video conferencing systems and automatic speech recognition systems. And more recently, dereverberation has been applied to hearing assistance devices such as hearing aids and cochlear implants.

State-of-the-art dereverberation algorithms usually implement estimation procedures to obtain relevant information for subsequent dereverberation and/or noise suppression processes. Since the estimation is exclusively based upon the audio signal captured by the system's general microphone, such algorithms are commonly referred to as "blind algorithms" in that they do not incorporate additional reference signals or a priori information about acoustic conditions (e.g. reverberation, background noise). Blind algorithms produce estimation errors which can actually decrease the perceptive signal quality below that of the original unprocessed audio signal. These algorithms also can be difficult to implement and parameterize—their performance represents a trade-off between computational complexity and energy consumption on one hand and estimation precision on the other.

Reverberation is typically conceived as having two parts: early reflections and late reverberation, and generally only the late reverberation is considered and modeled as an exponentially damped white Gaussian noise process. Blind estimation methods refer to the damping constant or decay rate of the modeling function, with either parameter being inversely proportional to the well-known room parameter, the reverberation time (RT60).

Ratnam et al., *Blind Estimation of Reverberation Time*, J. Acoust. Soc. Am., vol. 114(5), 2003 (incorporated herein by reference) proposed a maximum likelihood reverberation procedure using a subsequent order statistics filter as a post-processing stage for a continuous estimation process that does not require explicit detection of silence or speech-free signal parts. The estimator can be integrated into an automatic dereverberation process based on spectral subtraction. See also Löllmann and Vary, *Estimation of the Reverberation Time in Noisy Environments*, Proc. IWAENC, 2008, and Löllmann, and Vary, *A Blind Speech Enhancement Algorithm for the Suppression of Late Reverberation and Noise*, Proc. ICASSP, 2009, each of which is hereby incorporated herein by reference.

Wen et al., *Blind Estimation of Reverberation Time Based on the Distribution of Signal Decay Rates*, Proc. ICASSP, 2008 (incorporated herein by reference) incorporated a signal-offset detection algorithm for identifying regions with an almost freely decaying exponential envelope where the decay rate is calculated by a linear regression model in the energy domain. The reverberation time was then derived from the distribution of the decay rate estimates successively captured in a histogram. A similar method was proposed in Lopez et al., *Low Variance Blind Estimation of the Reverberation Time*, Proc. IWAENC, 2012 (incorporated herein by reference). Lebart and Boucher *A New Method Based on Spectral Subtraction for Speech Dereverberation*, Acta Acoustica, vol. 87, 2001 (incorporated herein by reference) directly estimated the decay rate through linear regression of the signal energy decay curve in speech-free regions. The pitch-based method of Wu and Wang, *A Pitch-Based Method for the Estimation of Short Reverberation Time*, Acta Acoustica, vol. 92, 2006 (incorporated herein by reference) evaluated the degree of corruption of the signal harmonic structure providing a measure of the reverberation time.

Figure 1:
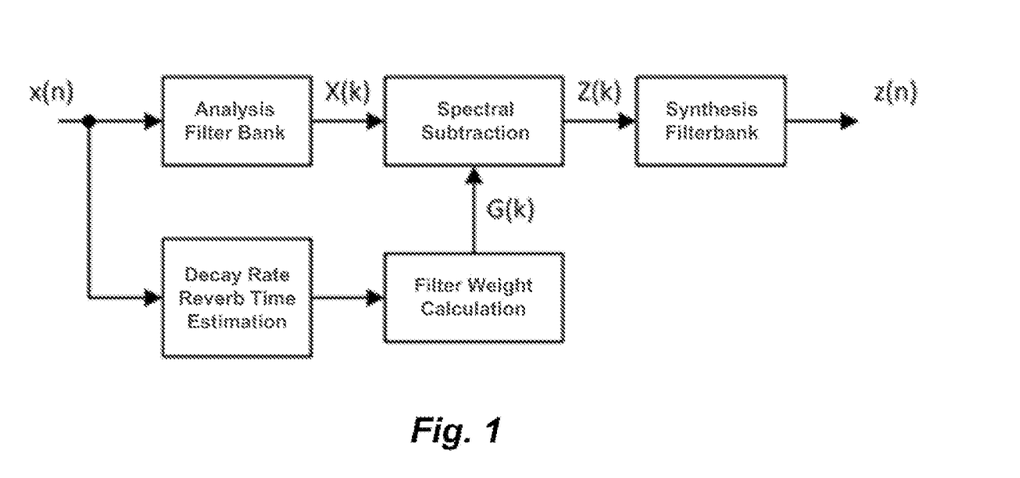
FIG. 1 shows functional blocks in a blind algorithm dereverberation process.
Figure 2:
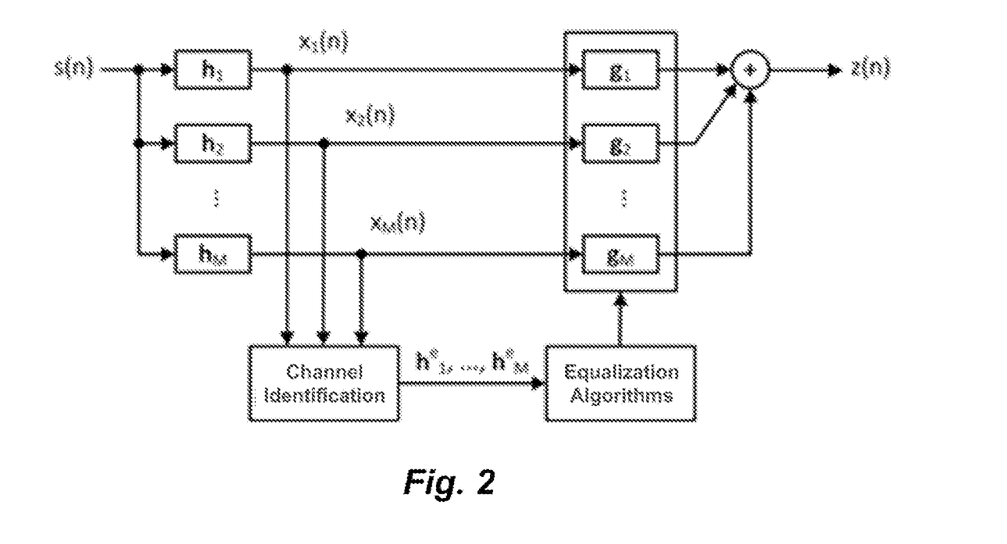
FIG. 2 shows functional blocks in an inverse filtering arrangement for dereverberation.

All of the foregoing estimator arrangements use the late reverberation signal-model and typically perform dereverberation by spectral subtraction in the short-time frequency domain as shown in FIG. 1. The original audio input signal x(n) is processed by an analysis filter bank to produce a frequency representation X(k). Spectral subtraction filter G(k) is applied to the frequency representation X(k) whereby the filter weights G(k) are derived from a decay rate and/or reverberation time estimate that also is produced from the audio input signal x(n). The dereverberated frequency representation Z(k) is then recombined by a synthesis filter bank to produce a dereverberated audio signal z(n). Significant research has also been spent on inverse filtering techniques as shown in FIG. 2, with the initial work presented in Miyoshi et al., *Inverse Filtering of Room Impulse Response*, Proc. IEEE ASSP 36, 1988 and Bees et al., *Reverberant Speech Enhancement Using Cepstral Processing*, Proc. ICASSP, 1991, both of which are incorporated herein by reference.

On the other hand, for some existing applications a priori room information is available and so the underlying signal processing need not employ a parameter estimator to handle the adverse effects of reverberation. Whereas blind algorithms are afflicted with estimation errors, the performance of dereverberation arrangements based on a priori information primarily depends upon how well the pre-defined room configurations match the actual real arrangement. Overviews of the most common state-of-the-art a priori approaches are given in Habets, *Single- and Multi Microphone Speech Dereverberation using Spectral Enhancement*, Ph.D. dissertation, Eindhoven Univ. of Technol., Eindhoven, The Netherlands, 2007 and Mosayybpour et al., *Single-Microphone Early and Late Reverberation Suppres-*

*sion in Noisy Speech*, IEEE Trans. on Audio, Speech, and Lang. Proc., vol. 21, no. 2, 2013, both of which are incorporated herein by reference.

U.S. Patent Publication 2009/0208043 describes a two-part system consisting of a beacon and a hearing assistance device, the former being used to create or capture acoustic codes of rooms and store them in a codebook. Both code and codebook are kept at a very simple basic level without providing any means for a comprehensive and extendable database. Furthermore, the codebook is locally stored on the user's device and so is not available to any other devices.

SUMMARY

Embodiments of the present invention are directed to hearing prosthesis arrangements for a hearing assisted patient. A microphone senses an acoustic environment around the hearing assisted patient and generates a corresponding microphone output signal. An audio signal processor processes the microphone output signal and produces a corresponding prosthesis stimulation signal to the patient for audio perception. The audio signal processor includes a dereverberation process that measures a dedicated reverberation reference signal produced in the acoustic environment to determine reverberation characteristics of the acoustic environment, and reduces reverberation effects in the hearing prosthesis stimulation signal based on the reverberation characteristics.

In specific embodiments, there may be a remote control separate from the audio signal processor and configured to produce the dedicated reverberation reference signal; for example, a hand held prosthesis remote control device. The dereverberation process may further redetermine the reverberation characteristics of the acoustic environment when the hearing assisted patient moves to a new location within the acoustic environment. This can automatically be performed by the dereverberation process by exploiting the patient's (i.e. audio processor's) position, or manually upon the patient's request (user control). And the hearing prosthesis stimulation signal may be a cochlear implant stimulation signal.

Embodiments of the present invention also are directed to hearing prosthesis arrangements for a hearing assisted patient. A microphone senses an acoustic environment around the hearing assisted patient and generates a corresponding microphone output signal. An audio signal processor processes the microphone output signal and produces a corresponding prosthesis stimulation signal to the patient for audio perception. The audio signal processor includes a dereverberation process that obtains environment-specific dereverberation data from an external database, and reduces reverberation effects in the hearing prosthesis stimulation signal based on the reverberation characteristics.

In further specific embodiments, the external database may be distributed across a plurality of external devices. Obtaining environment-specific dereverberation data from an external database may require satisfying one or more access restriction requirements of the external database. The dereverberation process may further redetermine the reverberation characteristics of the acoustic environment when the hearing assisted patient moves to a new location within the acoustic environment. And the hearing prosthesis stimulation signal may be a cochlear implant stimulation signal.

DETAILED DESCRIPTION

Various embodiments of the present invention are directed to hearing prosthesis arrangements for a hearing assisted patient that circumvent the problem of estimation errors in blind dereverberation algorithms by direct measurement of a reference reverberation signal produced in the acoustic environment. In the specific context of a hearing prosthesis system, the reference reverberation signal can be produced by a user remote control and then the reflected reference reverberation signal is measured by the sensing microphone in the system audio processor device.

Figure 3:
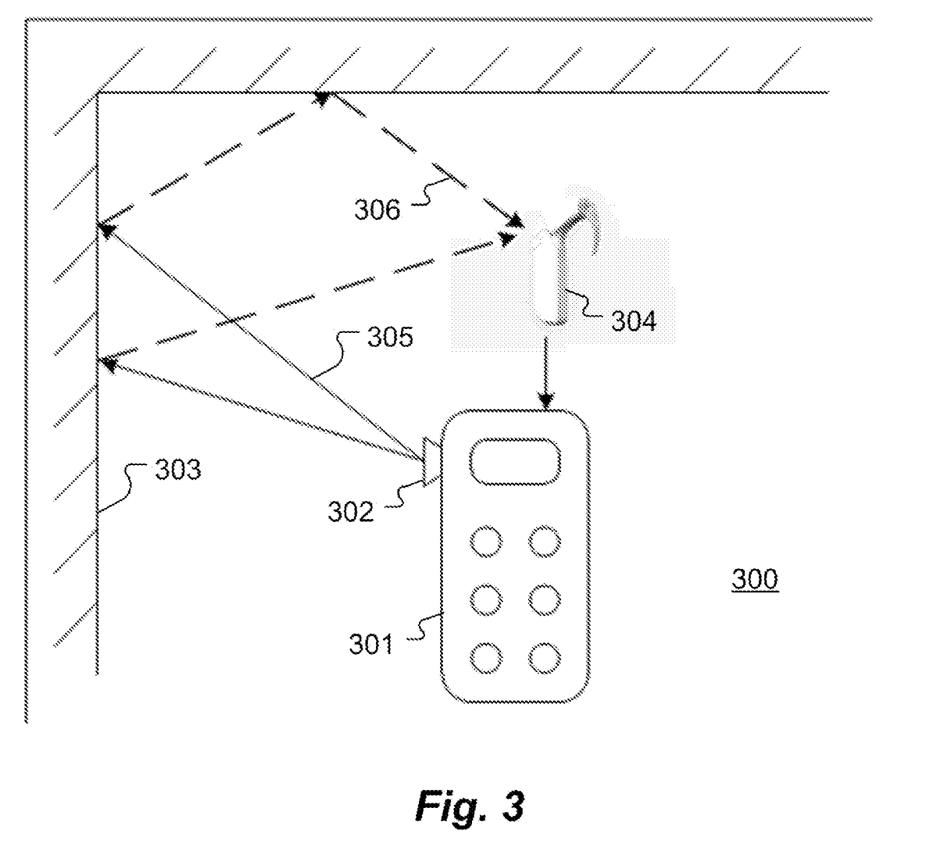
FIG. 3 shows a system for dereverberation using a reference reverberation signal according to an embodiment of the present invention.
Figure 4:
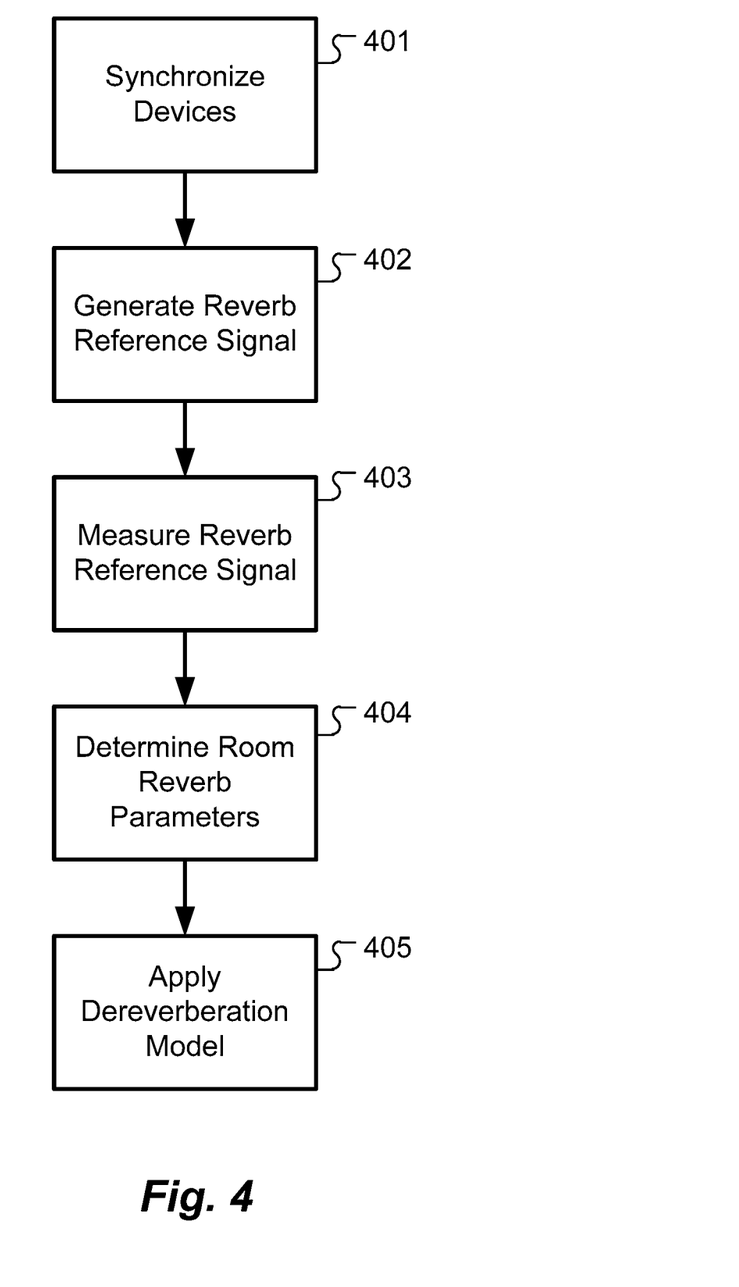
FIG. 4 shows various functional steps in a method of signal processing to reduce reverberation based on a reference reverberation signal.

FIG. 3 shows a system for reduced reverberation using a reference reverberation signal, and FIG. 4 shows various functional steps in such a method of signal processing. A behind the ear (BTE) device 304 of a hearing prosthesis system (e.g., a cochlear implant system) includes a sensing microphone that senses the acoustic environment 300 around a hearing impaired patient (i.e., the room where the patient is located). The BTE device 304 also contains an audio signal processor that processes the microphone output signal as an audio input signal and produces a corresponding prosthesis stimulation signal to the patient for audio perception, for example, by transcutaneous transmission of a cochlear implant stimulation signal to implanted components of a cochlear implant hearing prosthesis system. The hearing prosthesis system also includes a user remote control 301 that provides conveniently accessible user controls for user adjustment of the system. The remote control 301 also includes an audio output transducer 302 that can generate an audio output signal into the acoustic environment 300 (e.g., loudspeaker device).

Although FIG. 3 shows a BTE device 304 and a remote control 301 for a cochlear implant, embodiments of the invention are not limited to those specific devices. In other specific applications, other mobile devices can serve as audio signal sender and receiver (preferably two separated devices), which are equipped with a loudspeaker/audio output transducer and/or a sensing microphone and audio processing software. In fact, even non-mobile fixed sound processing systems such as Public Address (PA) systems, audio or video conferencing systems, and etc. may be used.

To reduce reverberation effects in the hearing prosthesis stimulation signal, the audio signal processor in the BTE device 304 and the remote control 301 initially are time synchronized, step 401, to begin a dereverberation process. The audio output transducer 302 in the remote control 301 then produces a dedicated reverberation reference signal 305 in the acoustic environment 300, step 402, that interacts with the structures in the acoustic environment 300, for example, reflecting off the walls 303.

A separate hardware device is time synchronized with the transmission of the reverberation reference signal 305 by the remote control 301 and measures the reflected reverberation reference signal 306, step 403, that contains acoustic information regarding the acoustic environment 300, i.e., room-specific features enabling improved audio signal processing that outperforms blind algorithms. In the embodiment shown in FIG. 3, the reflected reverberation reference signal 306 is measured by the BTE device 304 with its sensing microphone, and then the hearing system's audio processor within that device is conveniently available to perform the dereverberation processing. In addition, the location of the BTE device 304 with respect to the room geometry of the acoustic environment 300 is ideal for the purpose of dereverberation in the sense that it is also where the normal audio input signal for the system is sensed. Another advantage of conducting the dereverberation process using the audio processor in the BTE device 304 is that it is always available and ready-to-use; i.e. no hardware modification of existing processors is necessary. Still, other mobile audio recording devices may be used to perform the dereverberation process as long as the distance to the user's head is taken into account. Preserving this spatial arrangement is important, since the perceptive impression of reverberation is not constant within a room, but depends on the positions of the remote control 301 as audio source and the BTE device 304 as receiver. The inventors have found that instead of using the same device for transmission and reception of the reverberation reference signal 305, the reverberation parameters determined according to the invention are as good as and in various conditions better suited.

Time synchronization, step 401, may be established by a protocol sending a message between the BTE device 304 and the remote control 301 over a communication link, such as a wireless link. For example, the remote control 301 may send a start of transmission of the reverberation reference signal 305 to the BTE device 304. The BTE device upon reception of the message starts measuring the reflected reverberation reference signal 306 in step 403. In one embodiment, time synchronization, step 401, may be established by the BTE device 304 sending a message requesting transmission of the reverberation reference signal 305 to remote control 301. This allows that the BTE device 304 does not need to listen for messages from remote control 301 all the time and can keep the communication module in a sleep mode activated only during short transmission and/or reception periods to reduce power consumption.

The dereverberation process being run by the audio processor in the BTE device 304 determines reverberation characteristics of the acoustic environment, step 404, from the measured reflected reverberation reference signal 306. The reverberation characteristics typically are combined with other relevant reverberation information such as direct-to-reverberation ratio (DRR), reverberation time (RT60), etc. to form a dereverberation model that is applied to the operating audio input signal that is affected by reverberation, step 405, to calculate an estimate of the clean speech signal with reduced reverberation effects. It would further be useful to redetermine the reverberation characteristics of the acoustic environment 300 when the hearing assisted patient moves to a new location within the acoustic environment 300.

Using physically separated and separate devices to generate and send a clean reference signal with one of the devices and measure the reverberation reference signal with the other one of the devices has the advantage that the measured microphone output signal is not overshadowed by the much larger transmitted sound signal. This is particularly significant because the dynamic range of the sensing microphone is limited, and by not recording the large transmission signal component, the measurement of the reflected reverberation reference signal can be performed with better accuracy/resolution and the room reverberation can be better determined.

A typical real-life scenario for an embodiment of the invention might be a cochlear implant user who enters a room such as classroom or a church. The user would point the remote control in the direction of the teacher or minister, and press a button that causes the remote control to send out the dedicated reverberation reference signal. Especially in the classroom scenario, it is also easily possible to hand over the remote control to the teacher such that the clean signal is sent out at the position of the target signal (i.e. the voice of the teacher), which later is to be enhanced by the dereverberation procedure. The BTE device of the cochlear implant system then measures the reflected reverberation reference signal. In some embodiments, the BTE device might also receive a clean (unreflected) version of the transmitted reverberation reference by a wireless link from the remote control. Alternatively, the clean reference signal may already be stored in the BTE and provided to the remote control for sending out as a dedicated reverberation reference signal. The dereverberation process in the BTE device then calculates an estimate of the room reverberation from the clean reference and the measured reflected reverberation reference signal.

The patient user can evaluate and adjust the system performance to optimize the operation for the user. Such adjustments can be done, for example, during a fitting procedure with an experienced audiologist, or during actual usage of the system to adjust to different real life situations. This adjustment can be very useful since the measurement of the dereverberation could further lead to influence and change the stimulation processing.

It is known that if the input audio signal contains reverberation, channel-specific dereverberation information can be used as a stimulation selection criteria instead of or in combination with the band pass energy that is typically used. The acoustic reverberation information that is determined by the arrangement also can be applied exclusively or in combination with other channel-specific information (e.g., energy, signal-to-noise ratio SNR) as an input for an N-of-M selection process; or as an input for a carrier- and envelope-triggered cochlear stimulation strategy as for example described in U.S. Pat. No. 8,019,429B2 incorporated herein by reference to manipulate the threshold (e.g., lower threshold for less reverberations) or the filter coefficients (e.g., modify the slope of the gating signal depending on the reverberation information for calculating the threshold); or as an input for modifying the channel-specific inhibition time of a pulsatile implant stimulation as for example described in U.S. Pat. No. 8,417,348 to Schleich, which is incorporated herein by reference.

The stimulation coding strategy can evaluate and use the dereverberation information when it is beneficial. In an open-field (unenclosed) environment, the reverberation information is not relevant and need not be used to enhance the quality of the coding strategy. Under those conditions, a normal coding strategy is used.

Such arrangements for dereverberation in assisted hearing applications are highly accurate with improved adaptation to actual acoustic conditions. Predefined configurations can be exploited that provide computationally low complexity dereverberation with reduced estimation errors.

Embodiments of the present invention also are directed to hearing prosthesis arrangements for a hearing assisted patient with a dereverberation process based on incorporating a priori room information obtained from environment-specific dereverberation data from an external database.

Figure 5A:
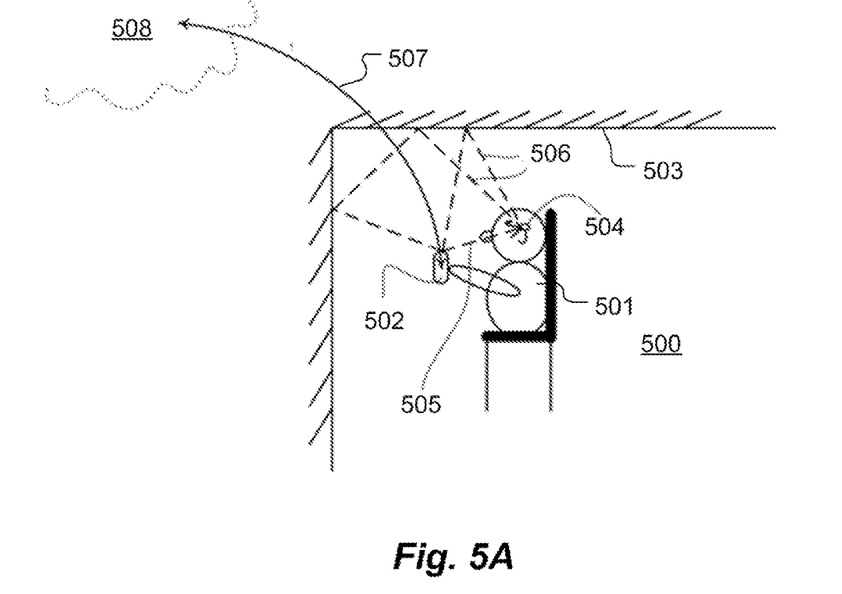
FIG. 5A-5B shows an arrangement for dereverberation using environment-specific dereverberation data from an external database according to an embodiment of the present invention.
Figure 5B:
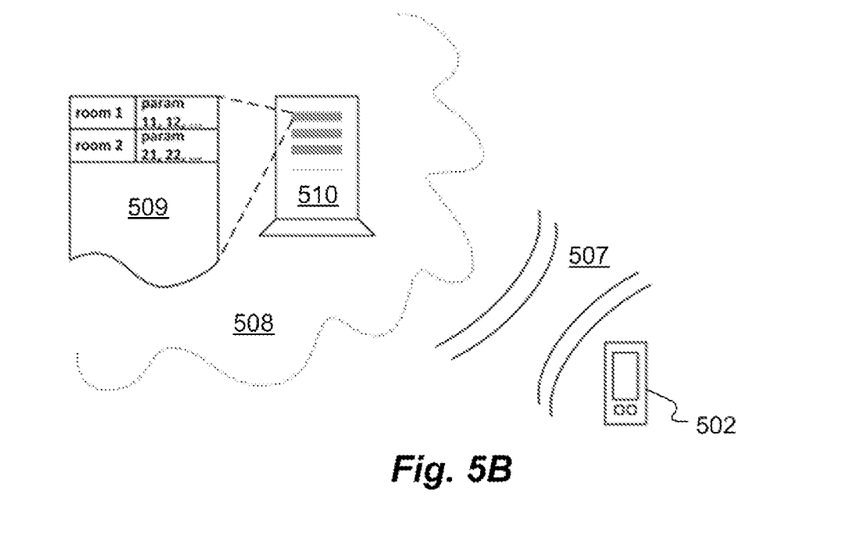
Figure 6:
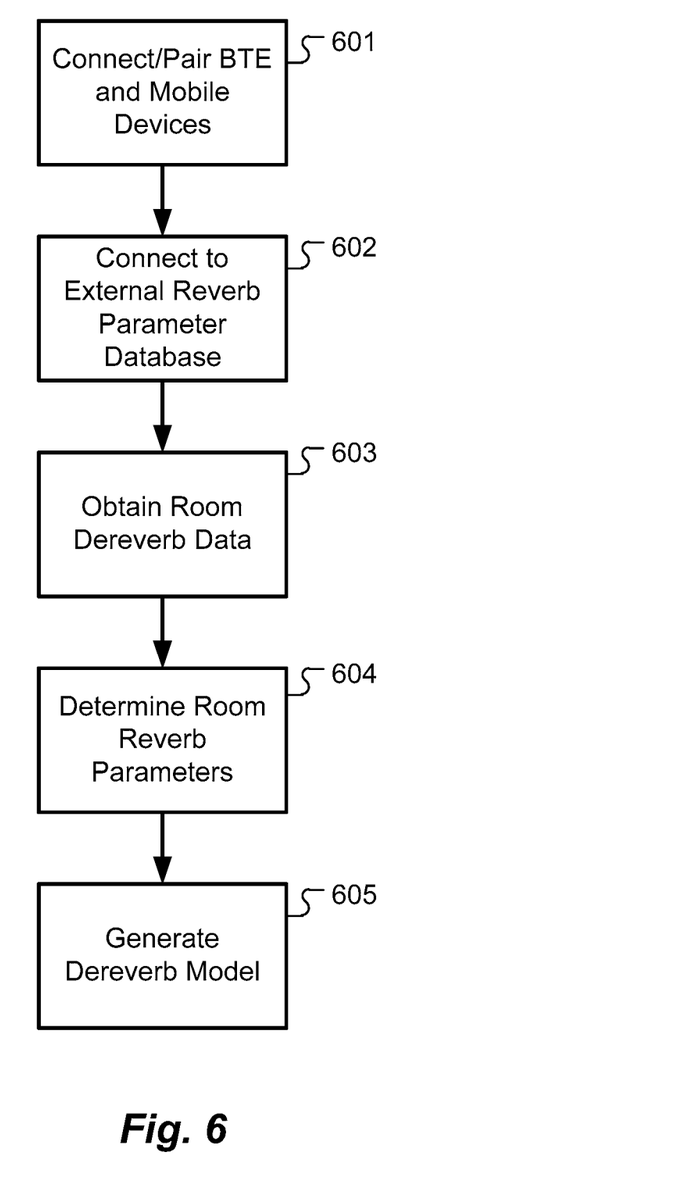
FIG. 6 shows various functional steps in a method of signal processing to reduce reverberation based on environment-specific dereverberation data from an external database.

FIG. 5A-5B shows a typical such embodiment and FIG. 6 shows various functional steps in such a method of signal processing. The patient user 501 is located in a room 500 that represents a specific acoustic environment. The patient user 501 has a mobile device 502 that includes a user interface with controls for user adjustment of the entire system including the dereverberation process. The mobile device 502 includes an audio output transducer (e.g., loudspeaker device) that can send out a clean reference signal 505 into the room 500 thereby resulting in a dedicated reverberation reference signal 506. The reflected reverberation reference signal 506 reflected from the walls 503 and other surfaces of the room 500 is sensed by a sensing microphone within a behind the ear (BTE) device 504 of a hearing prosthesis system (e.g., a cochlear implant system) worn by the hearing impaired patient user 501. The BTE device 504 also contains an audio signal processor that processes the microphone output signal as an audio input signal and produces a corresponding prosthesis stimulation signal to the patient for audio perception, for example, by transcutaneous transmission of a cochlear implant stimulation signal to implanted components of a cochlear implant hearing prosthesis system.

The mobile device 502 also provides access by wireless link 507 to a remote database server 510 in for example an internet cloud 508 which controls a reverberation parameter database 509 containing dereverberation data for different rooms/different acoustic environments. The reverberation parameter database 509 may be updated and extended continuously, i.e., any new room may be added to the database at any time, room acoustics changes may be updated as needed. Furthermore, the reverberation parameter database 509 may be one single large database or be a distributed, decentralised system. In either configuration, rooms having one or more common features may be clustered/categorised, e.g., rooms belonging to the same building (for example the class rooms of a school).

The dereverberation data in the reverberation parameter database 509 may be generated in various ways; for example, by direct acoustic measurements of the room to determine room impulse response measurements; by room simulations using computer program simulation software to calculate relevant room parameters, especially for missing parameters where some room response parameters are already available, by parameter mapping and completion between rooms—when the database entry of one room is incomplete but the information is sufficient to identify similar rooms in the reverberation parameter database 509, one or more missing parameters may be obtained by transformation, interpolation, extrapolation, pattern matching, averaging or likewise mathematical operations; and/or by employing both parameters of the desired room and those of similar rooms in room simulation software—for example, if a patient user enters a new room, he/she may estimate the room dimensions and a similar room type (e.g., office, class room, hall), already listed in the reverberation parameter database 509 may provide information about room acoustics (e.g., absorption coefficient, reverberation time). The patient user may also estimate and provide other relevant parameters for de-reverberation parameter estimation, such as e.g. the distance between the audio source and the listener (i.e., himself), or further details such as the positions of the audio source and the listener relative to the room walls.

Maintenance of the reverberation parameter database 509 may be restricted to a selected group of persons (e.g., database administrators), or patient users may be allowed to modify data in the reverberation parameter database 509. For example, a user taking a given location inside a room and using the de-reverberation process on any portable electronic device may use the same program/application to modify, fine tune, update, etc. specific room parameters, and afterwards pass (upload) the altered data set to the reverberation parameter database 509 in the database server 510. Any such database update process may be managed automatically and may include a plausibility check of the new/edited data parameters.

To reduce reverberation effects in the hearing prosthesis stimulation signal, the audio signal processor in the BTE device 504 and the mobile device 502 initially are connected or paired, step 601, and the mobile device 502 connects by the wireless link 507 to the reverberation parameter database 509 controlled by the remote database server 510 in the cloud 508, step 602. The database server 510 provides the room dereverberation data for that room 500 from the reverberation parameter database 509 via the wireless link 507 back to the mobile device 502, step 603. Obtaining the room dereverberation data may require satisfying one or more access restriction requirements (e.g., privacy controls limiting data access to approved users) of the reverberation parameter database 509. This permission-controlled data acquisition can be important particularly for private buildings. The mobile device 502 provides that reverberation data to the audio processor in the BTE device 504 which uses it to calculate room reverberation parameters, step 604, and generate a room dereverberation model, block 605. Alternatively, the mobile device 508 may itself calculate the relevant parameters for the de-reverberation process and may provide these parameters to the BTE device 504 via, e.g., a wireless link. Alternatively, the BTE device 504 can directly connect to the database server 510 by e.g. wireless link 507 to access the reverberation parameter database 509. The dereverberation model can be applied directly at the database server 510 which then returns to the BTE device 504 a corresponding prosthesis stimulation signal, or the database server 510 provides the room reverberation parameters to the to the BTE device 504 which includes the dereverberation model.

The dereverberation process run by the audio processor in the BTE device 504 determines reverberation characteristics of the room 500 to calculate an estimate of the clean speech signal with reduced reverberation effects. As with the earlier arrangement in FIG. 3, it may be useful to redetermine the reverberation characteristics of the room 500 when the patient user 501 moves to a new location within the room 500.

In different specific embodiments, the signal dereverberation processing can be performed at the remote database server 510, on the mobile device 502, on a tablet, a hearing system remote control, the BTE device 504, or some other external device.

There should be some provision made to correctly select the proper room database entry in the reverberation parameter database 509. In different specific embodiments, this can be done manually by the user, or by an automatic selection procedure. Some public buildings could be equipped with sensors that interact (i.e., exchange data) with the dereverberation processing software and/or the remote database server 510 automatically as soon as a user enters the room 500.

Figure 7:
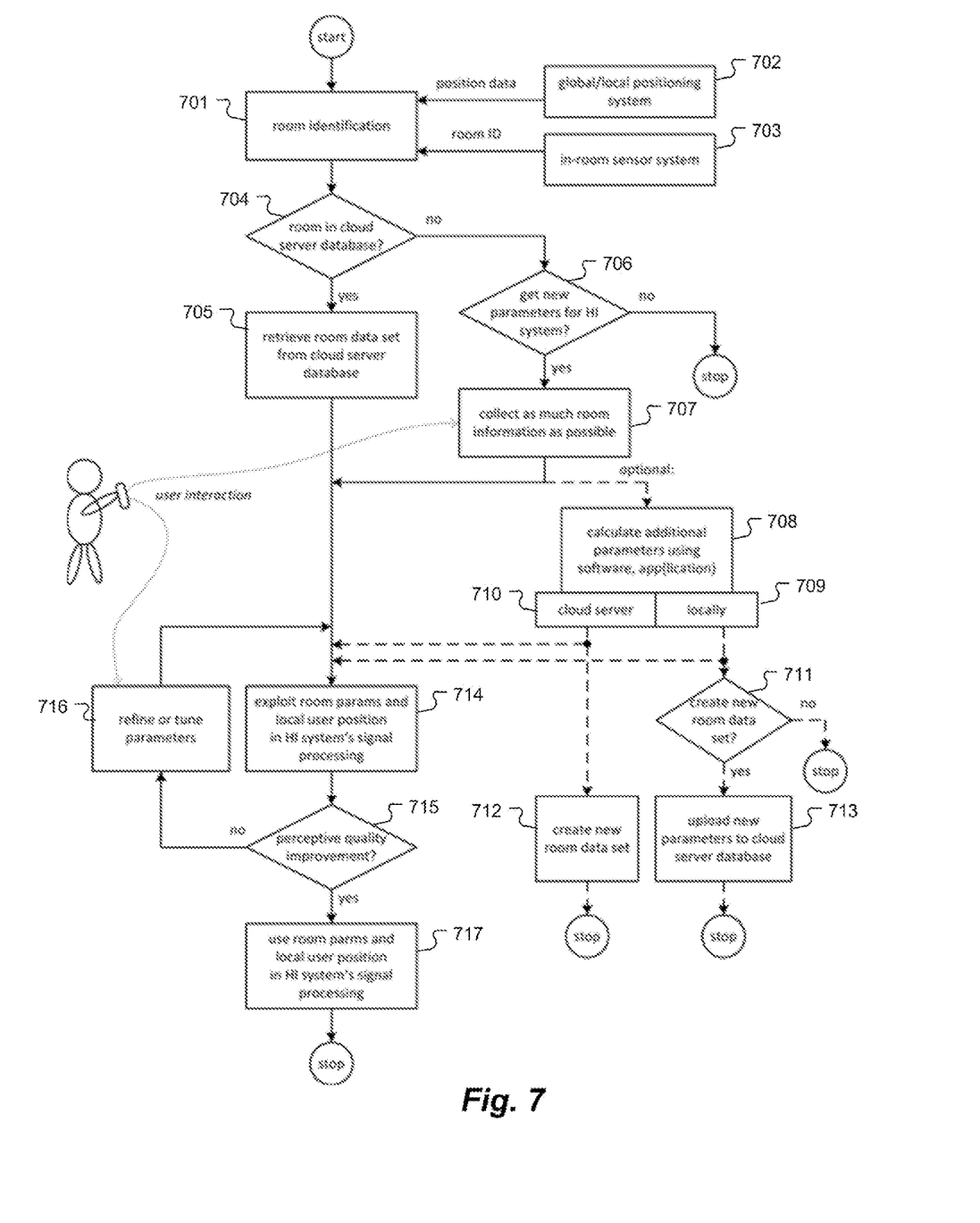
FIG. 7 shows detailed functional steps in a specific embodiment for reducing reverberation for a hearing prosthesis system.

FIG. 7 shows detailed functional steps in a specific embodiment for reducing reverberation for a hearing prosthesis system. When the system initially is exposed to a new acoustic environment, the room must first be identified, block 701, for example, based on position data from a global or local positioning system, block 702, and/or room identification data from an in-room sensor system, block 703. Once the room identification has been made, the algorithm accesses a cloud server reverberation database, block 704, typically using a wireless connection, and retrieves the data set for the room if it is in the database, block 705.

If the cloud server database does not have an existing data set for that specific room, the algorithm decides if such a room data set should be created, block 706. If not, the dereverberation process stops because no data is available, but otherwise, a new room data set can be created in the cloud server database by collecting as much room information as possible, block 707. That collected information can be used directly in further dereverberation processing, or it can be processed and used to calculate additional dereverberation parameters, block 708, and storing these locally, block 709, and/or globally in the cloud server, block 710. And again that additionally processed and calculated dereverberation parameter data can be used directly in further dereverberation processing, and/or serve to create a new room data set for storage in the cloud server, blocks 711, 712, and 713.

Whatever dereverberation data and parameters are available, are then exploited together with any available local user position data, block 714, for room-and user-specific dereverberation of the audio input signals to the hearing system. The system may then further check back with the user to determine if the dereverberation processing actually provides improved perceptive quality, block 715, and if not, the reverberation parameters and data may be refined further, block 716, until there is such an improvement in perception quality for which the system is stable and signal processing occurs using the existing data, block 717.

In specific embodiments, the data communication between the user and remote database may be realised as a simple computer program or an application for, e.g., a smart phone, a tablet, a laptop, or the remote control of the user's hearing device. Besides bi-directional data transfer of room parameters and/or audio signals, the communication between the hand-held (portable) device and the cloud server also may provide means for exchanging additional meta data. For example, one type of meta data denotes information about the actual location of the user within the room. In addition, the position of the primary sound source of the user's focus may also be useful. For example, during class in a classroom, a user pupil remains at his/her seat while the teacher who represents the desired speech source stays in front of the room around the desk and the blackboard. It can be useful to specify one or more secondary sound sources. Permanently installed or hand-held portable tracking systems (e.g., using optical tracking systems or other techniques) can be used to capture position information within a room with respect to room geometry as well as between the user and the sound source(s).

Embodiments of the invention may be implemented in part in any conventional computer programming language such as C, C++, C#, Java, VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A hearing prosthesis arrangement for a hearing assisted patient, the arrangement comprising:
   a first device including:
      a microphone configured to sense an acoustic environment around the hearing assisted patient and generate a corresponding microphone output signal; and
      an audio signal processor configured to process the microphone output signal and produce a corresponding hearing prosthesis stimulation signal to the hearing assisted patient for audio perception; and
   a remote control device separate from the first device, the remote control device configured to produce a dedicated reverberation reference signal in the acoustic environment, the remote control device and audio signal processor synchronizing timing of transmission of the dedicated reverberation reference signal by sending messages via a wireless communication link;
   wherein the audio signal processor includes a dereverberation process configured to:
      measure the dedicated reverberation reference signal produced and reflected in the acoustic environment, and sensed by the first device via the microphone, to determine reverberation characteristics of the acoustic environment, and reduce reverberation effects in the hearing prosthesis stimulation signal based on the reverberation characteristics.

2. The arrangement according to claim 1, wherein the remote control device is a hand held prosthesis remote control device.

3. The arrangement according to claim 1, wherein the dereverberation process further is configured to redetermine the reverberation characteristics of the acoustic environment when the hearing assisted patient moves to a new location within the acoustic environment.

4. The arrangement according to claim 1, wherein the hearing prosthesis stimulation signal is a cochlear implant stimulation signal.

5. A method of audio signal processing in a hearing prosthesis arrangement that includes:
   a microphone configured to sense an acoustic environment around the hearing assisted patient and generates a corresponding microphone output signal; and
   an audio signal processor configured to process the microphone output signal and produce a corresponding hearing prosthesis stimulation signal to the hearing assisted patient for audio perception,
   a remote control device separate from the first device, the remote control device configured to produce a dedicated reverberation reference signal, the remote control and audio signal processor synchronizing timing of transmission of the dedicated reverberation reference signal by sending messages via a wireless communication link;
   wherein the method comprises:
   using the audio signal processor to perform a dereverberation process comprising:
   measuring the dedicated reverberation reference signal produced and reflected in the acoustic environment, and sensed by the first device via the microphone, to determine reverberation characteristics of the acoustic environment, and
   reducing reverberation effects in the hearing prosthesis stimulation signal based on the reverberation characteristics.

6. The method according to claim 5, wherein the remote control device is a hand held prosthesis remote control device.

7. The method according to claim 5, wherein the dereverberation process further comprises redetermining the reverberation characteristics of the acoustic environment when the hearing assisted patient moves to a new location within the acoustic environment.

8. The method according to claim 5, wherein the hearing prosthesis stimulation signal is a cochlear implant stimulation signal.

* * * * *